US007160559B1

(12) United States Patent
McGee et al.

(10) Patent No.: US 7,160,559 B1
(45) Date of Patent: Jan. 9, 2007

(54) CONTROLLED RELEASE GALANTAMINE COMPOSITION

(75) Inventors: John Paul McGee, Antwerp (BE); Paul Marie Victor Gilis, Beerse (BE); Marc Maurice Germain De Weer, Vosselaar (BE); Valentin Florent Victor de Condé, Lommel (BE); Herman Johannes Catherina de Bruijn, Meer (BE); Frederic Anne Rodolf Van Dycke, Antwerp (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/868,991

(22) PCT Filed: Dec. 20, 1999

(86) PCT No.: PCT/EP99/10257

§ 371 (c)(1),
(2), (4) Date: Jul. 26, 2001

(87) PCT Pub. No.: WO00/38686

PCT Pub. Date: Jul. 6, 2000

(30) Foreign Application Priority Data

Dec. 24, 1998 (EP) .................................. 98204447

(51) Int. Cl.
*A61K 9/50* (2006.01)
*A61K 9/24* (2006.01)
*A61K 9/56* (2006.01)
*A61K 9/58* (2006.01)
*A61K 9/26* (2006.01)

(52) U.S. Cl. ..................... 424/501; 424/472; 424/459; 424/462; 424/469; 424/471

(58) Field of Classification Search ................ 514/215; 424/489, 490, 464, 465, 474, 468, 457, 472, 424/458, 459, 462, 469, 471, 501; 206/528, 206/532, 534, 539
See application file for complete search history.

(56) References Cited

U.S. PATENT DOCUMENTS

| 4,663,318 A | * | 5/1987 | Davis ......................... 514/215 |
| 5,151,273 A | | 9/1992 | Korsatko-Wabnegg et al. |
| 5,213,811 A | * | 5/1993 | Frisbee et al. .............. 424/451 |
| 5,519,017 A | | 5/1996 | Opitz |
| 5,576,022 A | * | 11/1996 | Yang et al. .................. 424/472 |
| 5,589,475 A | | 12/1996 | Snorrason |
| 5,643,905 A | | 7/1997 | Moormann |
| 6,183,777 B1 | * | 2/2001 | Chen et al. .................. 424/472 |
| 6,273,260 B1 | * | 8/2001 | ColDepietro et al. ..... 206/459.5 |

FOREIGN PATENT DOCUMENTS

| CA | 1 326 632 | | 2/1994 |
| CA | 1326632 | * | 2/1994 |
| EP | 0648771 A1 | | 4/1995 |
| EP | 0653427 B1 | | 5/1995 |
| EP | 0879596 A2 | | 11/1998 |
| JP | 6-507617 | | 9/1994 |
| JP | 9-165329 | | 6/1997 |
| JP | 9-295933 | | 11/1997 |
| JP | 10-231242 | | 9/1998 |
| WO | 88 08708 | | 11/1988 |
| WO | WO 97/03987 | | 2/1997 |
| WO | WO 97/47304 | | 12/1997 |
| WO | WO 98/22072 | * | 5/1998 |
| WO | WO 98/55148 | | 12/1998 |
| WO | WO 99/21561 | | 5/1999 |
| WO | WO 00/38686 | | 7/2000 |
| WO | WO 00/30446 A1 | | 8/2000 |
| WO | WO 0051970 | | 9/2000 |

OTHER PUBLICATIONS

Chiao, C.S.L., et al. "Sustained-Release Drug Delivery Systems." Remington: The Science and Practice of Pharmacy, Gennaro, A.R., ed. 1995, pp. 1660 & 1661.
Conte, U, et al. Press Coated Tablets For Time-Programmed Release Of Drugs, Biomaterials. 1993, vol. 14, No. 13 pp. 1017-1023, Entire Document.
Goodman & Gilman's The Pharmacological Basis of Therapeutics, Ninth Edition, pp. 161-176, Chapter 8 (eds. Joal G. Hardman and Lee E. Limbird, McGraw-Hill, 1996).

* cited by examiner

*Primary Examiner*—Michael Hartley
*Assistant Examiner*—Blessing Fubara
(74) *Attorney, Agent, or Firm*—Mary A. Appollina

(57) ABSTRACT

The present invention is concerned with controlled release compositions for oral administration comprising galantamine; and with processes of preparing such controlled release compositions.

15 Claims, No Drawings

CONTROLLED RELEASE GALANTAMINE COMPOSITION

This application is a National Stage application under 35 U.S.C. 371 of Application No. PCT/EP99/10257 filed Dec. 20, 1999, which claims priority from EP 98204447.1, filed Dec. 24, 1998, the contents of all of which are hereby incorporated by reference.

The present invention is concerned with controlled release compositions for oral administration comprising galantamine; and with processes of preparing such controlled release compositions.

Galantamine (I), a tertiary alkaloid, has been isolated from the bulbs of the Caucasian snowdrops *Galanthus woronowi* (Proskumina, N. F. and Yakoleva, A. P. 1952, Alkaloids of *Galanthus woronowi*. II. Isolation of a new alkaloid. (In Russian.) Zh. Obschchei Khim. (J. Gen. Chem.) 22, 1899–1902). It has also been isolated from the common snowdrop *Galanthus nivalis* (Boit, 1954).

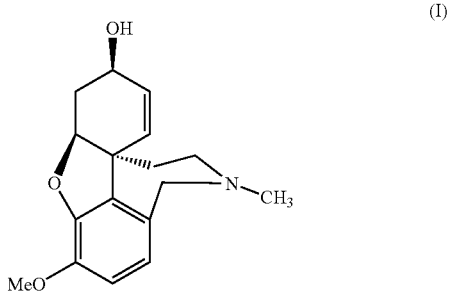

The chemical name of galantamine is [4aS-(4aα, 6β, 8aR*)]-4a, 5, 9, 10, 11, 12-hexahydro-3-methoxy-11-methyl-6H-benzofuro[3a, 3, 2-ef][2]benzazepin-6-ol; both the base compound and its hydrobromide are laevorotatory. Galantamine is a well-known acetylcholinesterase inhibitor which is active at nicotinic receptor sites but not on muscarinic receptor sites. It is capable of passing the blood-brain barrier in humans, and presents no severe side effects in therapeutically effective dosages.

Galantamine has been used extensively as a curare reversal agent in anaesthetic practice in Eastern bloc countries (cf. review by Paskow, 1986) and also experimentally in the West (cf. Bretagne and Valetta, 1965: Wislicki, 1967; Consanitis, 1971).

Galantamine has been marketed by Waldheim (Sanochemia Gruppe) as Nivalin™ in Germany and Austria since the 1970s for indications such as facial neuralgia.

The use of galantamine or an analogue or a pharmaceutically acceptable acid addition salt thereof for the preparation of a medicament for treating Alzheimer's Dermentia (AD) and related dementias has been described in EP-0,236,684 (U.S. Pat. No. 4,663,318). This patent only has a generic disclosure of possible dosage forms of galantamine. CA-1,326,632 generically discloses slow release formulations of galantamine.

The use of galantamine for treating alcoholism and the administration via a transdermal therapeutic system (TTS) or patch is disclosed in EP-0,449,247 and WO-94/16707. Similarly, the use of galantamine in the treatment of nicotine dependence using administration via a transdermal therapeutic system (TTS) or patch is disclosed in WO-94/16708. Treatment of nerve gas poisoning is disclosed in DE-4,342,174.

A number of applications by E. Snorrason disclose the use of galantamine, analogues thereof and pharmaceutically acceptable salts thereof for the preparation of medicaments for treating mania (U.S. Pat. No. 5,336,675), chronic fatigue syndrome (CFS) (EP-0,515,302; U.S. Pat. No. 5,312,817), the negative effects of benzodiazepine treatment (EP-0,515,301) and the treatment of schizophrenia (U.S. Pat. No. 5,633,238). In these applications and patents, e.g. in U.S. Pat. No. 5,312,817, a number of immediate release tablet formulations of galantamine hydrobromide are given.

WO-97/47304 discloses fast-dissolving or immediate release tablets of galantamine prepared by direct compression. These and other art-known immediate release tablets are administered twice (b.i.d.) or thrice (t.i.d.) daily with an interval of 8 hours. The plasma levels of the active ingredient typically raise sharply (early $T_{max}$ and relatively high $C_{max}$) and decline rapidly (deep trough after about 6 to 8 hours).

Therapy with galantamine can be considered optimal when effective plasma levels are reached when required. In addition, peak values ($C_{max}$) should be as low and level as possible so as to reduce the incidence and severity of possible side effects. The foregoing requirements not only apply upon single dose administration, but also upon repeated dose administration (until a steady-state condition is reached). In particular, when treating a patient suffering from Alzheimer's Disease, optimum efficacy is expected when effective plasma levels are maintained during daytime; during nighttime galantamine plasma levels probably may be lower. For the treatment of other conditions, for example for treating sleep disordered breathing such as snoring and apnoea (WO-97/22339), one may wish to attain the reverse situation, namely to have effective plasma levels during the night, and lower levels during daytime. For the benefit of the patient and the caretakers, a pharmaceutical dosage form that has to be administered once daily only and yields effective plasma levels for eight hours (nighttime) to 16 hours (daytime) would be highly desirable.

The present invention relates to a controlled release formulation containing galantamine as the active ingredient, characterized in that it comprises particles comprising galantamine or a pharmaceutically acceptable acid addition salt thereof, a water soluble pharmaceutically acceptable excipient and optionally other pharmaceutically acceptable excipients, said particles being coated by a release rate controlling membrane coating. Dosage forms comprising a therapeutically effective amount of said controlled release formulations can be administered orally to a patient once daily. In preferred dosage forms, part of the galantamine is present in an immediate release form, for example, as particles lacking a release rate controlling membrane coating, or as immediate release minitablets, or as as a topcoat on the controlled release formulation.

Preferably, the formulations according to the present invention comprise galantamine in the form of galantamine hydrobromide (1:1).

The water soluble excipient can conveniently be a film forming polymer. Useful water soluble film forming polymers are polymers that have an apparent viscosity of 1 to 100 mPa.s when dissolved in a 2% aqueous solution at 20° C. solution. For example, the water soluble polymer can be selected from the group comprising alkylcelluloses such as methylcellulose, hydroxyalkylcelluloses such as hydroxymethylcellulose, hydroxyethylcellulose, hydroxypropylcellulose and hydroxybutylcellulose, hydroxyalkyl alkylcelluloses such as hydroxyethyl methylcellulose and hydroxypropyl methylcellulose,
carboxyalkylcelluloses such as carboxymethylcellulose,
alkali metal salts of carboxyalkylcelluloses such as sodium carboxymethyl-cellulose,
carboxyalkyl alkylcelluloses such as carboxymethyl ethylcellulose,
carboxyalkylcellulose esters,
starches,
pectines such as sodium carboxymethylamylopectine,
chitine derivates such as chitosan,
polysaccharides such as alginic acid, alkali metal and ammonium salts thereof, carrageenans, galactomannans, traganth, agar-agar, gummi arabicum, guar gummi and xanthan gummi,
polyarcylic acids and the salts thereof,
polymethacrylic acids and the salts thereof, methacrylate copolymers,
polyvinylalcohol,
polyvinylpyrrolidone, copolymers of polyvinylpyrrolidone with vinyl acetate
polyalkylene oxides such as polyethylene oxide and polypropylene oxide and copolymers of ethylene oxide and propylene oxide.

Non-enumerated polymers which are pharmaceutically acceptable and have appropriate physico-chemical properties as defined hereinbefore are equally suited for preparing particles according to the present invention.

Preferred water-soluble polymers are for example hydroxypropyl methylcellulose (Methocel®, Pharmacoat®, polymethacrylate (Eudragit E®), hydroxypropylcellulose (Klucel®, or a polyvidone. Especially preferred water-soluble polymers are hydroxypropyl methylcelluloses or HPMC. Said HPMC contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule. Hydroxypropyl methylcellulose is the United States Adopted Name for hypromellose (see Martindale, The Extra Pharmacopoeia, 29th edition, page 1435). Preferably hydroxypropyl methylcellulose with low viscosity, i.e. about 5 mPa.s, is used, e.g. hydroxypropyl methylcellulose 2910 5 mPa.s. In the four digit number "2910", the first two digits represent the approximate percentage of methoxyl groups and the third and fourth digits the approximate percentage composition of hydroxypropoxyl groups. 5 mPa.s is a value indicative of the apparent viscosity of a 2% aqueous solution at 20° C.

Suitable HPMC include those having a viscosity from about 1 to about 100 mPa.s, in particular form about 3 to about 15 mPa.s, preferably about 5 mPa.s The most preferred type of HPMC having a viscosity of 5 mPa.s., is the commercially available HPMC 2910 5 mPa.s. An equally preferred type of HPMC is admixed with polyethylene glycol 400, commercially available from Colorcon (UK) as Opadry™ OY-7240 clear.

The weight-by-weight ratio of drug:polymer is in the range of 17:1 to 1:5, preferably 10:1 to 1:3. In the case of (galantamine.HBr):(HPMC 2910 5 mPa.s), said ratio may range from about 10:1 to about 1:3, and optimally is from 7:1 to 1:2. The weight-by-weight ratio of galantamine.HBr to other water-soluble polymers may be determined by a person skilled in the art by straightforward experimentation. The lower limit is determined by practical considerations.

In particular the present invention is concerned with particles which comprise (a) a central, rounded or spherical core, (b) a layer or a coating film of a water-soluble polymer and galantamine hydrobromide (1:1), (c) optionally a seal-coating polymer layer and (d) a release rate controlling membrane coating. The core has a diameter of about 250 to about 1,180 µm (16–60 mesh), preferably of about 600 to about 1,180 µm (16–30 mesh).

Pellets, beads or cores of the dimensions mentioned herein can be obtained by sieving through nominal standard test sieves as described in the CRC Handbook, 64th ed., page F-114. Nominal standard sieves are characterized by the mesh/hole width (µm), DIN 4188 (mm), ASTM E 11-70 (No), Tyler® (mesh) or BS 410 (mesh) standard values. Throughout this description and the claims, particle sizes are designated by reference to the mesh/hole width in µm and to the corresponding Sieve No in the ASTM E11-70 standard.

Materials suitable for use as cores in the particles according to the present invention are manifold, provided that said materials are pharmaceutically acceptable and have appropriate dimensions (about 16–60 mesh) and firmness. Examples of such materials are polymers e.g. plastic resins; inorganic substances, e.g. silica, glass, hydroxyapatite, salts (sodium or potassium chloride, calcium or magnesium carbonate) and the like; organic substances, e.g. activated carbon, acids (citric, fumaric, tartaric, ascorbic and the like acids), and saccharides and derivatives thereof. Particularly suitable materials are saccharides such as sugars, oligosaccharides, polysaccharides and their derivatives, for example, glucose, rhamnose, galactose, lactose, sucrose, mannitol, sorbitol, dextrin, maltodextrin, cellulose, microcrystalline cellulose, sodium carboxymethyl cellulose, starches (maize, rice, potato, wheat, tapioca) and the like saccharides.

A particularly preferred material suitable for use as cores in the particles according to the present invention is represented by 16–60 mesh sugar spheres (USP 22/NF X VII, p. 1989) which consist of 62.5%–91.5% (w/w) sucrose, the remainder being starch and possibly also dextrines, and which are pharmaceutically inert or neutral. Consequently, these cores are also known in the art as neutral pellets.

Depending on the weight-by-weight ratio of drug:polymer, the water-soluble polymer and galantamine are herein said to form either a layer (ratio >10:1) or a coat or coating film (ratio <10:1).

As an alternative to the drug layered or drug coated inert pellets described thus far, suitable particles comprising glantamine may also be formed by granules or by spheroids (spherical granules) prepared according to art-known methods of granulation and spheronization.

The release rate controlling membrane coating comprises a water insoluble polymer and optionally a plasticizer. Said polymer is ethylcellulosee and the plasticizer is selected from the group comprising dibutyl sebacate, diethyl phthalate and triethyl citrate. It is useful to modify the properties of the water-insoluble polymer by the addition of particular amounts of a water-soluble polymer as described hereinbefore, preferably HPMC. The addition of the water-soluble polymer is especially useful to increase the onset of action. For the particles according to the present invention, the ratio ethylcellulose:HPMC can vary from 100:0 to about 70:30, in particular from about 80:20 to about 72.5–27.5, more in particular from about 75:25 to about 72.5:27:5. The release rate controlling membrane coating may be applied to the drug coated cores in an aqueous dispersion (Aquacoat™, Surelease™), or as a solution in an organic solvent system. A useful organic system comprises an alcohol, e.g. methanol or ethanol, and optionally a chlorinated hydrocarbon such as for example dichloromethane.

The weight of the release rate controlling membrane coating ranges from 3% to 15% of the uncoated particle, in particular from about 4% to about 12%. The rate of release of the active ingredient from the particles is approximately inversely proportional with the thickness of the release rate controlling membrane coating.

A seal coat lies optionally between the drug core and the release rate controlling membrane coating. The seal coating polymer layer is applied to the drug coated cores to prevent sticking of the particles during the process and to prevent migration of the drug into the the release rate controlling membrane. Preferably, a thin layer of HPMC 2910 5 mPa.s and polyethylene glycol (PEG), in particular polyethylene glycol 400 is used as a seal coating polymer layer.

In addition, the particles according to the present invention may further contain various additives such as thickening agents, lubricants, surfactants, preservatives, complexing and chelating agents, electrolytes or other active ingredients.

The particles can be filled in hard-gelatin capsules such that a therapeutically effective amount of, for example, 8 to 32 mg of the active ingredient is available per dosage form. An advantageous pharmacokinetic profile profile (fast onset, level peak and trough values) is obtained when from 70 to 80% of the galantamine is comprised within the controlled release particles and the remaining 20 to 30% of the galantamine is comprised in an immediate release form, preferably the controlled releases particle amount to 75% of the galantamine and the immediate release form to 25%.

In order to achieve the desired pharmacokinetic, the dosage forms may be filled with particles that release the active ingredient at different rates, at least one kind that releases the active ingredient slowly, and at least one kind that releases the active ingredient more rapidly, in particular one kind that releases the active ingredient immediately, e.g. particles as described that lack the release rate controlling membrane. The different particles may be filled consecutively in the capsules, or they may be premixed and the thus obtained premix may be filled into the capsules (taking into account possible segregation).

Alternatively, the controlled release particles of the present invention may further comprise a top-coat of a water-soluble polymer as described hereinbefore and galantamine which is released practically immediately upon ingestion and thus ensures a rapid onset of action.

Another alternative solution for providing a dosage form with a pharmacokinetic profile as outlined, namely with a fast onset, level peak and trough values, comprises filling a capsule with controlled release particles as described hereinbefore (70 to 80%, preferably 75% of the galantamine dose) together with one or more minitablets which comprise the remaining 20 to 30%, preferably 25% of galantamine. Suitable immediate release tablet formulations of galantamine have been described previously in WO-97/47304.

The present invention also relates to processes of preparing formulations as described hereinbefore comprising admixing galantamine or a pharmaceutically acceptable salt form thereof with a water soluble excipient to form a drug core, optionally applying a seal coat to the drug core, and thereafter applying the release rate controlling membrane coating.

The particles according to the present invention are conveniently prepared in the following manner. A drug coating solution is prepared by dissolving into a suitable solvent system appropriate amounts of galantamine.HBr and a water-soluble polymer. A suitable solvent system comprises purified water or an alcohol, preferably ethanol which may be denatured, for example, with butanone. The amounts of solids, i.e. galantamine.HBr and water-soluble polymer, in the drug coating solution may range from 10 to 30% (w/w) and preferably is about 25%. The solution is preferably stirred during the coating process.

The drug coating process (on an industrial scale) is conveniently conducted in a fluidized bed granulator (e.g. Glatt type WSG-30 or GPCG-30) equipped with a Wurster bottom spray insert (e.g. an 18 inch Wurster insert). Laboratory scale process development can be performed on a Glatt type WSG-1 with a 6 inch Wurster bottom insert. Obviously the process parameters depend on the equipment used.

The spraying rate should be regulated carefully. Too low a spraying rate can cause some spray drying of the drug coating solution and result in a loss of product. Too high a spraying rate will cause overwetting with subsequent agglomeration. Agglomeration being the most serious problem, lower spraying rates may be used initially, to be increased as the coating process proceeds and the particles grow larger.

The atomizing air pressure with which the drug coating solution is applied also influences the coating performance. Low atomizing air pressure results in the formation of larger droplets and an increased tendency toward agglomeration. High atomizing air pressure could conceivably carry the risk of spray drying the drug solution, but this was found not to be a problem. Consequently, atomizing air pressure may be set at nearly maximum levels.

Fluidizing air volume can be monitored by operating the exhaust air-valve of the apparatus and should be set in such a manner that optimum pellet circulation is obtained. Too low an air volume will cause insufficient fluidization of the pellets; too high an air volume will interfere with the pellet circulation due to countercurrent air streams developing in the apparatus. In the present process optimum conditions were obtained by opening the exhaust air valve to about 50% of its maximum and gradually increasing the opening thereof to about 60% of the maximum as the coating process proceeded.

The coating process is advantageously conducted by employing an inlet-air temperature ranging from about 50° C. to about 55° C. Higher temperatures may speed up the process but have the disadvantage that solvent evaporation is so rapid that the coating liquid is not spread uniformly on the surface of the pellets resulting in the formation of a drug coating layer with high porosity. As the bulk volume of the coated pellets increases, drug dissolution may decrease significantly to unacceptable levels. Obviously, the optimum process temperature will further depend on the equipment used, the nature of the core, the batch volume, the solvent and the spraying rate.

Parameter settings for optimum coating results are described in more detail in the example hereinafter. Running the coating process under those conditions was found to yield very reproducible results.

In order to decrease residual solvent levels in the pellets following application of the rate controlling membrane from an organic solution, the pellets can conveniently be dried in any suitable drying apparatus. Good results may be obtained using a vacuum tumbler-drier operated at a temperature from about 60° C. to about 90° C., preferably about 80° C., a reduced pressure ranging from about 150–400 mbar (15–40 kPa), preferably 200–300 mbar (20–30 kPa), for at least 24 hours, preferably about 36 hours. The vacuum tumbler-drier is conveniently rotated at its minimum speed, e.g. 2 to 3 rpm. After drying, the drug coated cores may be sieved.

The seal coat layer is applied to the drug coated cores in the fluidized bed granulator with Wurster bottom spray insert or in a powder coater. The seal coating solution can be prepared by dissolving an appropriate amount of a seal coating polymer into a suitable solvent system. Such a system, is, e.g. purified water or an alcohol, preferably ethanol which may be denatured with, for example, butanone. The amount of seal coating polymer in the seal coating spraying solution may range from 5 to 10% (w/w) and preferably is about 6.6%. The seal coating spraying solution is advantageously stirred during the seal coating process. Appropriate conditions are described in more detail in the example hereinafter.

A further drying step may be required after applying the seal coating polymer layer. Excess solvents could easily be removed while operating the apparatus at the parameter settings used for about 5 to 15 minutes after the spraying had been completed.

The release rate controlling membrane coating polymer layer is applied to the drug (or seal) coated cores in a fluidized bed granulator with Wurster bottom spray insert. The release rate controlling membrane coating suspension or solution can be prepared by suspending or dissolving an appropriate amount of a release rate controlling membrane coating polymer into a suitable solvent system. Such a system, is, e.g. purified water or an alcohol, preferably ethanol which may be denatured with, for example, butanone, dichloromethane which may be admixed with an alcohol, preferably methanol or ethanol. The amount of release rate controlling membrane coating polymer in the spraying suspension or solution may range from 5 to 40% (w/w) and preferably is about 30%. The release rate controlling membrane coating spraying suspension or solution is advantageously stirred during the spraying process. The parameter setting for conducting this last step is essentially similar to that used in the previous coating processes. Appropriate conditions are described in more detail in the example hereinafter.

All coating processes are preferably conducted under an inert atmosphere of e.g. nitrogen. The coating equipment should preferably be grounded and provided with an appropriate solvent recovery system containing an efficient condensing system.

The particles may be filled in hard-gelatin capsules using standard automatic capsule filling machines. Suitable earthing and de-ionisation equipment can advantageously prevent development of electrostatic charges.

Capsule filling speed may influence weight distribution and should be monitored. Good results are obtained when operating the equipment at about 75% to 85% of the maximum speed and in many cases when operating at full speed.

Dosage forms according to the present invention having an advantageous pharmacokinetic profile as outlined, namely a fast onset and level peak and trough values, are capable of releasing in 500 ml USP buffer (pH 6.8) at 37° C. in an Apparatus 2 (USP 23, <711> Dissolution, pp 1791–1793, paddle, 50 rpm) from 20 to 40% of the total amount of galantamine.HBr in 1 hour, and more than 80% of the total amount of galantamine.HBr in 10 hours. Said dosage forms provide a mean maximum plasma concentration of galantamine from 10 to 60 ng/ml and a mean minimum plasma concentration from 3 to 15 ng/ml after repeated administration every day through steady-state conditions.

The formulation according to the present invention deliver a therapeutically effective amount of galantamine to a patient during the 24 hours following a single once daily administration.

The present invention also concerns pharmaceutical packages suitable for commercial sale comprising a container, a formulation of galantamine as claimed in claim 1, and associated with said package written matter specifying how said formulation should be administered.

Said pharmaceutical packages may be adapted for titrating a patient who is 'acetylcholine esterase inhibitor'-naïve, i.e. a patient who has not been exposed to an acetylcholine esterase inhibitor before and who should start with small, well-tolerated doses before being exposed to ever higher doses until the optimal dose is reached. Said packages typically comprises 21–35 daily sequential dosage units of (a) a first group of 7 to 14 dosage units comprising from 5 to 10 mg galantamine, (b) a second group of 7 to 14 dosage units comprising from 10 to 20 mg galantamine, (c) a third group of 7 to 14 dosage units comprising from 15 to 30 mg galantamine, and (d) optionally a fourth group of 7 dosage units comprising from 20 to 40 mg galantamine.

Alternatively, the pharmaceutical packages may be adapted for treating a patient who is 'acetylcholine esterase inhibitor'-tolerant, i.e. a patient who has been exposed to an acetylcholine esterase inhibitor before and who tolerate an optimal dose. Said packages typically comprises daily dosage units comprising from 15 to 30 mg galantamine.

A method of treating Alzheimer's dementia and related dementias in a human while substantially reducing (avoiding) the concomitant liability of adverse effects associated with acetyl cholinesterase inhibitors, comprising administering to a human in need of such treatment, a therapeutically effective amount of galantamine in a controlled release formulation as claimed in claim 1, said amount being sufficient to alleviate said Alzheimer's dementia and related dementias, but insufficient to cause said adverse effects.

The related dementia belongs to the group consisting of vascular dementia, Lewy body disease, autism, mental retardation, bipolar disorder psychiatric conditions, disruptive behaviour, attention deficit hyperactivity disorder, substance abuse, extreme aggression, especially conduct disorder, nicotine cessation and withdrawal.

The adverse effects belong to the group comprising nausea, vomiting, sweating, restlessness, and insomnia.

Experimental part
Example 1: 8 mg galantamine CR oral capsule (F1)

Ingredients:

| | |
|---|---|
| galantamine hydrobromide | 10.253 mg (8 mg galantamine base) |
| sugar spheres (18–20 mesh) | 63.283 mg |
| HPMC 2910 5 mPa · s | 1.465 mg |
| purified water | 37.105 µl * |
| HPMC 2910 5 mPa · s | 1.500 mg |
| polyethylene glycol 400 | 0.150 mg |
| purified water | 23.350 µl * |
| ethylcellulose aqueous dispersion | 10.220 mg (30%) |

Experimental part
Example 1: 8 mg galantamine CR oral capsule (F1)

-continued

Ingredients:

| | |
|---|---|
| dibutyl sebacate | 0.736 mg |
| purified water | 10.220 μl * |
| capsule nr. 4 | |

*: these ingredients do not occur in the end product

Preparation:

a) Drug coat suspension

Galantamine hydrobromide (123 g) was suspended in 297 ml purified water and heated to 70–80° C. HPMC 2910 5 mPa.s (17.58 g) was dissolved in the heated supension whilst stirring.

b) Seal coat solution

Purified water (93.4 g) was heated to 70–80° C. and HPMC 2910 4 mPa.s (18 g) and polyethylene glycol 400 (1.8 g) were dissolved therein. The solution was then further diluted with purified water (186.8 g).

c) Release rate controlling membrane coat dispersion

To a gently stirred aqueous dispersion of ethylcellulose (122.6 g; 30%) was added dibutyl sebacate (8.832 g). The dispersion was diluted with purified water (122.6 g).

d) Coating process

A fluidized-bed granulator (Glatt, type WSG 1) equipped with a 6 inch Wurster (bottom spray) insert was loaded with 18–20 mesh sugar spheres (759.4 g). The spheres were warmed with dry air of about 50° C. The fluidizing air volume was controlled by opening the exhaust air valve to approximately 45% of its maximum. The drug coat suspension was sprayed on the spheres moving in the apparatus. The suspension was sprayed at a delivery rate of about 5 to 30 g.min$^{-1}$ at an atomizing air pressure of about 1.6 to 4.0 bar (0.16–0.4 MPa). When the spraying process was completed, the coated spheres were dried by further supplying dry air of 60° C. for about 2 minutes. The coated spheres were then seal coated with the sealcoat solution using the same parameters as used in the drug coating process. After drying for about 2 minutes, the seal coated spheres were allowed to cool to room temperature and filled into a stainless steel drum.

The fluidized-bed granulator (Glatt, type WSG 1) equipped with a 6 inch Wurster (bottom spray) insert was reloaded with the seal coated spheres. The spheres were warmed with dry air of about 50° C. The fluidizing air volume was controlled by opening the exhaust air valve to approximately 45% of its maximum. The release rate controlling membrane coat suspension was sprayed on the spheres moving in the apparatus. The suspension was sprayed at a delivery rate of about 5 to 30 g.min$^{-1}$ at an atomizing air pressure of about 1.6 to 4.0 bar (0.16–0.4 MPa). After drying for about 2 minutes, the controlled release membrane coated spheres were allowed to cool to room temperature and filled into a stainless steel drum.

e) Drying and curing process

In order to remove agglomerates, the coated spheres were sieved using a sieve having a mesh width of 1.2 mm. The particles were placed in a drying oven at 60° C. during 2 hours so as to cure the release rate controlling membrane.

f) Capsule filling

The particles were filled into hard-gelatin capsules (size 4) using standard automatic capsule filling machines (e.g. Model GFK-1500, Höffliger and Karg. Germany). In order to obtain capsules with good weight distribution, capsule filling speed was reduced to about 75–85% of the maximum speed. Each capsule received approximately 87.6 mg particles, equivalent to about 8 mg galantamine.

Example 2: 8 mg galantamine CR oral capsule (F2)

Ingredients:

| | |
|---|---|
| galantamine hydrobromide | 10.253 mg (8 mg galantamine base) |
| sugar spheres (18–20 mesh) | 63.283 mg |
| HPMC 2910 5 mPa · s | 1.465 mg |
| purified water | 37.105 μl * |
| HPMC 2910 5 mPa · s | 1.500 mg |
| polyethylene glycol 400 | 0.150 mg |
| purified water | 23.350 μl * |
| ethylcellulose aqueous dispersion | 25.550 mg (30%) |
| dibutyl sebacate | 1.840 mg |
| purified water | 25.550 μl * |
| capsule nr. 4 | |

*: these ingredients do not occur in the end product

The preparation was identical to that described in Example 1 except for the preparation of the release rate controlling membrane dispersion.

c) Release rate controlling membrane coat dispersion

To a gently stirred aqueous dispersion of ethylcellulose (306.6 g; 30%) was added dibutyl sebacate (22.08 g). The dispersion was diluted with purified water (306.6 g).

Example 3: Bioavailability

The bioavailability of a single oral administration of the two controlled release formulations of examples 1 and 2 was compared with that of an immediate release tablet (F3) [WO-97/47304] comprising 4 mg galantamine which was administered twice daily with an interval of 8 hours. Galantamine plasma levels in healthy volunteers (12) were determined by HPLC and the mean values calculated from the individual measurements are reported in the following table.

| time (h) | F1 | F2 | F3 |
|---|---|---|---|
| 0 | nd | nd | nd |
| 0.5 | 1.6 | nd | 16.4 |
| 1 | 7.3 | nd | 24.1 |
| 1.5 | 11.5 | nd | 20.3 |
| 2 | 16.3 | 1.8 | 18.3 |
| 3 | 23.8 | 3.7 | 16.9 |
| 4 | 26.7 | 6.3 | 14.5 |
| 6 | 25.2 | 9.5 | 11.3 |
| 8 | 22.5 | 10.5 | 9.3 |
| 8.5 | | | 18 |
| 9 | | | 24.5 |
| 9.5 | | | 25.5 |
| 10 | 18.6 | 11.1 | 23.7 |
| 11 | | | 22.7 |
| 12 | 15.1 | 12.0 | 19.3 |
| 14 | 13.4 | 12.4 | 15.2 |
| 16 | 10.8 | 11.7 | 12.7 |
| 24 | 6.0 | 8.8 | 6.6 |
| 30 | 3.5 | 6.1 | 3.5 |
| 36 | 2.0 | 4.3 | 2.0 |
| 48 | nd | 1.6 | nd | nd: not detectable (<1 ng/ml)

Example 4: oral capsule (F4) comprising 8 mg galantamine
(75% CR pellets and 25% IR tablet)

Ingredients:

| | |
|---|---|
| sugar spheres (18–20 mesh) | 63.482 mg |
| galantamine hydrobromide | 7.69 mg (6 mg galantamine base) |
| HPMC 2910 5 mPa · s | 0.641 mg |
| purified water | 42.932 μl * |
| HPMC 2910 5 mPa · s | 1.436 mg |
| polyethylene glycol 400 | 0.145 mg |
| methylene chloride | 12.385 μl * |
| ethanol 96% (v/v) | 10.858 mg * |
| HPMC 2910 5 mPa · s | 1.101 mg |
| ethylcellulose 20 mPa · s | 3.308 mg |
| diethyl phthalate | 0.881 mg |
| methylene chloride | 31.077 μl * |
| ethanol 96% (v/v) | 27.244 mg * |
| galantamine hydrobromide | 2.563 mg (2 mg galantamine base) |
| spray-dried mixture of lactose monohydrate and microcrystalline cellulose (75:25) | 49.302 mg |
| colloidal anhydrous silica | 0.11 mg |
| crospolyvidone | 2.750 mg |
| magnesium stearate | 0.275 mg |

*: these ingredients do not occur in the end product

Preparation:

a) Drug layer suspension

Galantamine hydrobromide was suspended in purified water and heated to 70–80° C. HPMC 2910 5 mPa.s was dissolved in the heated supension whilst stirring.

b) Seal coat solution

Methylene chloride and ethanol were mixed together and polyethylene glycol and HPMC 2910 5 mPa.s were dissolved therein.

c) Release rate controlling membrane coat solution

Methylene chloride and ethanol were mixed and ethylcellulose 20 mPa.s, HPMC 2910 5 mPa.s and diethyl phtalate were added while stirring the solution.

d) Layering and coating process

A fluidized-bed granulator (Glatt) equipped with a Wurster (bottom spray) insert was loaded with 18–20 mesh sugar spheres. The spheres were warmed with dry air of about 50° C. The fluidizing air volume was controlled by opening the exhaust air valve to approximately 45% of its maximum. The drug layer suspension was sprayed on the spheres moving in the apparatus When the spraying process was completed, the layered spheres were dried by further supplying dry air of 60° C. for about 2 minutes. The layered spheres were then seal coated with the seal coat solution using the same parameters as used in the drug coating process. After drying for about 2 minutes, the seal coated spheres were allowed to cool to room temperature and filled into a stainless steel drum.

The fluidized-bed granulator (Glatt) equipped with a Wurster (bottom spray) insert was reloaded with the seal coated spheres. The spheres were warmed with dry air of about 50° C. The fluidizing air volume was controlled by opening the exhaust air valve to approximately 45% of its maximum. The release rate controlling membrane coat suspension was sprayed on the spheres moving in the apparatus. After drying for about 2 minutes, the controlled release membrane coated spheres were allowed to cool to room temperature, sieved and filled into a stainless steel drum.

e) Immediate release minitablet

Galantamine hydrobromide, spray-dried mixture of lactose monohydrate and microcrystalline cellulose (75:25), colloidal anhydrous silica, crospolyvidone and magnesium stearate were mixed in a planetary mixer and compressed in a tabletting machine, thus preparing minitablets of 55 mg weight.

f) Capsule filling

The coated spheres and the immediate release minitab were filled into hard-gelatin capsules (size 0) using standard automatic capsule filling machines (e.g. Model GFK-1500, Höffliger and Karg. Germany).

Example 5: galantamine oral capsules (F5, F6, F7, F8)
(75% CR pellets and 25% IR topcoat)

Ingredients:

| | |
|---|---|
| sugar spheres (18–20 mesh) | 63.624 mg |
| galantamine hydrobromide | 7.69 mg (6 mg galantamine base) |
| HPMC 2910 5 mPa · s and PEG 400 | 12.687 mg (Opadry™ OY-7240 Clear, Colorcon) |
| purified water | 267.693 μl * |
| HPMC 29105 mPa · s | 1.260 mg |
| ethylcellulose 20 mPa · s | 3.780 mg |
| diethyl phthalate | 1.008 mg |
| methylene chloride | 46.772 μl * |
| ethanol 96% (v/v) | 31.184 mg * |
| galantamine hydrobromide | 2.563 mg (2 mg galantamine base) |
| HPMC 2910 5 mPa · s and PEG 400 | 4.229 mg (Opadry OY-7240 Clear) |
| purified water | 89.321 μl * |
| capsules size nr. 4, 2, 1 and 0. | |

*: these ingredients do not occur in the end product

Preparation:

a) Drug coat solution

Galantamine hydrobromide and Opadry OY-7240 Clear were dissolved in purified water at room temperature.

b) Release rate controlling membrane coat solution

Methylene chloride and ethanol were mixed and ethylcellulose 20 mPa.s, PHMC 2910 5 mPa.s and diethyl phtalate were added while stirring the solution.

c) Drug topcoat solution

Galantamine hydrobromide and Opadry™ OY-7240 Clear were dissolved in purified water at room temperature.

d) Coating process

A fluidized-bed granulator (Glatt) equipped with a Wurster (bottom spray) insert was loaded with 18–20 mesh sugar spheres. The spheres were warmed with dry air of about 50° C. The fluidizing air volume was controlled by opening the exhaust air valve to approximately 45% of its maximum. The drug coat solution was sprayed on the spheres moving in the apparatus. When the spraying process was completed, the coated spheres were dried by further supplying dry air of 60° C. for about 2 minutes. The release rate controlling membrane coat solution was sprayed on the spheres moving in the apparatus. After drying for about 2 minutes, the controlled release membrane coated spheres were sprayed with the drug topcoat solution. After drying for about 2 minutes, the topcoated spheres were allowed to cool to room temperature, sieved and were filled into a stainless steel drum.

e) Capsule filling

The topcoated spheres (96.841 mg; 193.683 mg; 290.524; 387.365 mg) were filled into hard-gelatin capsules (size numbers 4, 2, 1, 0) using standard automatic capsule filling machines (e.g. Model GFK-1500, Höffliger and Karg. Germany) yielding oral capsules containing respectively 8 mg, 16 mg, 24 mg and 32 mg galantamine base.

Example 6: Galantamine oral capsules (F9) (75% CR pellets and 25% IR topcoat)

Spheres having slightly faster release were made by lowering the ratio of ethylcellulose 20 mPa.s to HPMC 2910 5 mPa.s to 72.5:27.5 (as compared to the ratio 75:25 in the previous example.

Example 7: In vitro dissolution of the topcoated spheres

Comparative in-vitro dissolutions studies were performed on the topcoated spheres formulations F5 to F8 and F9. The medium was 500 ml of USP buffer pH 6.8 at 37° C. in Apparatus 2 (USP 23, <711> Dissolution, pp. 1791–1793) (paddle, 50 rpm). The following results were obtained:

| | Calculated concentration (% w/w) of the active dose | | | | | | |
|---|---|---|---|---|---|---|---|
| Time (min) | sample 1 | sample 2 | sample 3 | sample 4 | sample 5 | sample 6 | average |
| | | | F5 to F8 | | | | |
| 0 | 0.00 | 0.00 | 0.00 | 0.00 | 0.00 | 0.00 | 0.00 |
| 60 | 32.20 | 30.44 | 37.47 | 30.44 | 30.44 | 38.05 | 33.17 |
| 120 | 42.54 | 41.37 | 48.39 | 41.37 | 42.54 | 42.54 | 43.13 |
| 240 | 58.93 | 60.10 | 65.96 | 61.27 | 61.27 | 61.27 | 61.47 |
| 480 | 85.47 | 80.20 | 84.30 | 81.96 | 81.37 | 80.79 | 82.35 |
| 720 | 91.52 | 90.35 | 97.37 | 99.13 | 92.11 | 87.42 | 92.98 |
| 1080 | 96.59 | 97.18 | 102.45 | 102.45 | 99.52 | 98.94 | 99.52 |
| 1410 | 96.40 | 97.57 | 103.42 | 103.42 | 100.5 | 101.08 | 100.40 |
| | | | F9 | | | | |
| 0 | 0.00 | 0.00 | 0.00 | 0.00 | 0.00 | 0.00 | 0.00 |
| 60 | 38.9 | 36.0 | 36.5 | 39.5 | 33.4 | 37.2 | 32.86 |
| 120 | 60.3 | 55.7 | 56.9 | 60.4 | 60.9 | 55.1 | 58.2 |
| 240 | 89.5 | 81.8 | 86.2 | 86.7 | 91.2 | 84.0 | 86.6 |
| 480 | 103.4 | 103.6 | 95.9 | 101.7 | 100.8 | 105.8 | 101.9 |
| 720 | 107.0 | 99.0 | 104.0 | 103.1 | 109.1 | 100.8 | 103.8 |

The invention claimed is:

1. A controlled release formulation containing galantamine as the active ingredient, characterized in that it comprises particles comprising galantamine hydrobromide (1:1), and a water soluble film forming polymer wherein the galantamine hydrobromide (1:1) and the water soluble film forming polymer are layered or coated on inert spheres, said particles being coated by a release rate controlling membrane coating wherein the release rate controlling membrane coating comprises a water insoluble polymer and optionally a plasticizer, and wherein the formulation further comprises a topcoat comprising galantamine and water-soluble polymer and wherein the formulation is capable of releasing in USP buffer pH 6.8 at 37° C. in a paddle apparatus operating at 50 rpm, from 20 to 40% of the total amount of galantamine.HBr in 1 hour, and more than 80% of the total amount of galantamine.HBr in 10 hours.

2. A formulation according to claim 1 wherein the water insoluble polymer is ethylcellulose and the plasticizer is selected from the group consisting of dibutyl sebacate, diethyl phthalate and triethyl citrate.

3. A formulation according to claim 2 wherein the weight of the release rate controlling membrane coating ranges from 3% to 15% of the uncoated particle.

4. A formulation according to claim 1 wherein a seal coat lies between the drug core and the release rate controlling membrane coating.

5. A formulation according to claim 1 wherein the water soluble film forming polymer is a polymer that has an apparent viscosity of 1 to 100 mPa.s when dissolved in a 2% aqueous solution at 20° C. solution.

6. A formulation according to claim 5 wherein the water soluble polymer is selected from the group consisting of
   alkylcelluloses such as methylcellulose,
   hydroxyalkylcelluloses such as hydroxymethylcellulose, hydroxyethylcellulose,
   hydroxypropylcellulose and hydroxybutylcellulose,
   hydroxyalkyl alkylcelluloses such as hydroxyethyl methylcellulose and hydroxypropyl methylcellulose,
   carboxyalkylcelluloses such as carboxymethylcellulose,
   alkali metal salts of carboxyalkylcelluloses such as sodium carboxymethylcellulose,
   carboxyalkylalkylcelluloses such as carboxymethylethylcellulose,
   carboxyalkylcellulose esters,
   starches,
   pectines such as sodium carboxymethylamylopectine,
   chitine derivatives such as chitosan,
   polysaccharides such as alginic acid, alkali metal and ammonium salts thereof, carrageenans, galactomannans, traganth, agar-agar, gummi arabicum, guar gummi and xanthan gummi,
   polyacrylic acids and the salts thereof,
   polymethacrylic acids and the salts thereof, methacrylate copolymers,
   polyvinylalcohol,
   polyvinylpyrrolidone, copolymers of polyvinylpyrrolidone with vinyl acetate
   polyalkylene oxides such as polyethylene oxide and polypropylene oxide and copolymers of ethylene oxide and propylene oxide.

7. A formulation according to claim 6 wherein the water soluble polymer is hydroxypropyl methylcellulose HPMC 2910 with an apparent viscosity of 5 mPa.s when dissolved in a 2% aqueous solution at 20° C.

8. A formulation according to claim 7 wherein the weight-by-weight ratio of said hydroxypropyl methylcellulose to galantamine is in the range of 17:1 to 1:5.

9. A formulation according to claim 1 wherein the inert spheres are 16–60 mesh (1,180–250 μm) sugar spheres.

10. A formulation according to any of claim 5, 6, 7, 8, 9 or 4 which delivers a therapeutically effective amount of galantamine to a patient during the 24 hours following a single once daily administration.

11. A formulation according to claim 1 providing a mean maximum plasma concentration of galantamine from 10 to 60 ng/ml and a mean minimum plasma concentration from 3 to 15 ng/ml after repeated administration every day through steady-state conditions.

12. A process of preparing a formulation according to claim 1 comprising admixing galantamine hydrobromide (1:1) with a water soluble film forming polymer and coating onto inert spheres to form a drug core, optionally applying a seal coat to the drug core, applying the release rate controlling membrane coating, and thereafter applying a topcoat comprising galantamine and a water-soluble polymer.

13. A method of treating Alzheimer's dementia in a human while substantially reducing or avoiding the concomitant liability of adverse effects associated with acetyl cholinesterase inhibitors, comprising administering to a human in need of such treatment, a therapeutically effective amount of galantamine in a controlled release formulation as claimed in claim 1, said amount being sufficient to alleviate said Alzheimer's dementia, but insufficient to cause said adverse effects.

14. A method according to claim 13 wherein the adverse effects belong to the group comprising nausea, vomiting, sweating, restlessness, and insomnia.

15. A formulation according to claim 1, wherein the particles are filled in a hard-gelatin capsule.

* * * * *